(12) United States Patent
Petry et al.

(10) Patent No.: US 7,453,000 B2
(45) Date of Patent: Nov. 18, 2008

(54) SUBSTITUTED OXAZOLOBENZOISOTHIAZOLE DIOXIDE DERIVATIVES METHOD FOR PRODUCTION AND USE THEREOF

(75) Inventors: Stefan Petry, Kelkheim (DE); Norbert Tennagels, Siegburg (DE); Reinhard Kirsch, Braunschweig (DE); Karl-Heinz Baringhaus, Wolfersheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/560,602

(22) Filed: Nov. 16, 2006

(65) Prior Publication Data

US 2007/0149511 A1    Jun. 28, 2007

Related U.S. Application Data

(63) Continuation of application No. PCT/EP2005/005321, filed on May 14, 2005.

(30) Foreign Application Priority Data

May 29, 2004    (DE) .................. 10 2004 026 532

(51) Int. Cl.
C07D 275/04    (2006.01)
A01N 43/80     (2006.01)
(52) U.S. Cl. ....................... 548/207; 514/373
(58) Field of Classification Search ........................ None
See application file for complete search history.

(56) References Cited

FOREIGN PATENT DOCUMENTS

| WO | WO 92/05164 | 4/1992 |
| WO | WO 01/74812 | 10/2001 |
| WO | WO 02/11722 | 2/2002 |
| WO | WO 2005012295 | * 2/2005 |

OTHER PUBLICATIONS

Sparks et al., "Benzothiazole benzimidazole (s) isothiazolidinone derivatives as protein tyrosin phosphatase-1B inhibitors", Bioorg. Med Chem Lett, 17, 2007, 736-740.*
Wan et al., "Probing acid replacements of thiophene PTP1B inhibitors", Bioorg. Med Chem Lett, 17, 2007, 2913-2920.*
Geneara, http://www.genaera.com/pressreleases/August%208,%202007.pdf.*
Collins, Expert Opinion Investig. Drugs 2007, 16(11), 1743-1751.*
Alzheimer's Disease Treatment Phases, http://www.alzheimerstreatment.org/treatment/disease-treatment.htm.*
Alzheimer's Drugs, Consumer Reports Best Buy Drugs (p. 1-5).*
Xue et al., J. Biol. Chem., 282 (2007), 23829-23840.*
A Successor to Herceptin?, http://www.telegraph.co.uk/connected/main.jhtml?xml=/connected/2007/01/29/echep29.xml, 2 pages.*

* cited by examiner

Primary Examiner—Kamal Saeed
Assistant Examiner—Sun Jae Y Loewe
(74) Attorney, Agent, or Firm—Craig M. Bell

(57) ABSTRACT

The invention relates to compounds of formula (I), where the groups have the meanings set forth herein and the physiologically-acceptable salts thereof. The compounds are suitable as medicaments for lowering blood sugar levels and for prevention and treatment of diabetes.

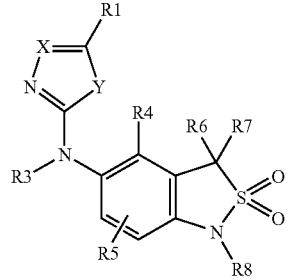

9 Claims, No Drawings

SUBSTITUTED OXAZOLOBENZOISOTHIAZOLE DIOXIDE DERIVATIVES METHOD FOR PRODUCTION AND USE THEREOF

CROSS-REFERENCE TO RELATED APPLICATIONS

This application is a continuation of PCT/EP2005/005321, filed 14 May 2005, which claims priority from DE (German) Patent Application No. 10 2004 026 532.1, filed 29 May 2004.

SUMMARY OF THE INVENTION

The invention relates to substituted oxazole-benzoisothiazole dioxide derivatives and the physiologically tolerated salts thereof.

BACKGROUND OF THE INVENTION

Benzoisothiazole dioxide derivatives of similar structure have been described in the prior art, as has the use thereof for the treatment of diabetes (WO 02/11722).

The invention was based on the object of providing compounds with which it is possible to prevent and treat diabetes mellitus. For this purpose, the compounds were intended to display a therapeutically utilizable blood glucose-lowering effect. In particular, the compounds were intended to show an improved effect or an improved ADME profile (absorption, distribution, metabolism and excretion) compared with the compounds of WO 02/11722.

DETAILED DESCRIPTION OF THE INVENTION

The invention therefore relates to compounds of the formula I

I in which the meanings are

X O, C—R2;
Y O, C—R2,
it always being the case that one of the groups X and Y is equal to O and the other is equal to C—R1;

R1, R2 independently of one another H, aryl, COOH, ($C_1$-$C_6$)-alkylene-COOH, —COO($C_1$-$C_6$)-alkyl, ($C_1$-$C_6$)-alkylene-COO($C_1$-$C_6$)-alkyl, ($C_1$-$C_6$)-alkyl, ($C_2$-$C_6$)-alkenyl, ($C_1$-$C_6$)-alkylene-aryl, heterocycle, ($C_1$-$C_6$)-alkylene-heterocycle, $CF_3$, $OCF_3$, CN, ($CH_2$)$_{1-6}$—OH, O—($C_1$-$C_6$)-alkyl, CO—($C_1$-$C_6$)-alkyl, —C(O)O-alkyl, COOH, CON(R9)(R10), where the aryl radicals and the heterocyclic radicals may be substituted one or more times by F, Cl, Br, ($CH_2$)$_{0-2}$OH, ($C_1$-$C_6$)-alkyl, ($C_2$-$C_6$)-alkenyl, ($C_2$-$C_6$)-alkynyl, $CF_3$, $OCF_3$, N(R9)(R10), piperidinone, piperazine, piperazinone, N—($C_1$-$C_6$-alkylene)-piperazine, N—($C_1$-$C_6$-alkylene)-piperazinone, morpholine, thiomorpholine, $NO_2$, CN, O—($C_1$-$C_6$)-alkyl, $S(O)_{0-2}$—($C_1$-$C_6$)-alkyl, $SO_2$—N(R9)(R10), CO—($C_1$-$C_6$)-alkyl, —COOH, ($C_1$-$C_6$)-alkylene-COOH, COO($C_1$-$C_6$)-alkyl, ($C_1$-$C_6$)-alkylene-COO($C_1$-$C_6$)-alkyl, ($C_3$-$C_{10}$)-cycloalkyl, phenyl, where these piperidinone, piperazine, piperazinone, N—($C_1$-$C_6$-alkylene)-piperazine, N—($C_1$-$C_6$-alkylene)-piperazinone, morpholine, thiomorpholine and phenyl rings may be substituted one or more times by F, Cl, Br, ($CH_2$)$_{0-2}$OH, COOH, CN, $NO_2$, —O—($C_1$-$C_6$)-alkyl, —NH—O—($C_1$-$C_6$)-alkyl, —(CO)—NH—O—($C_1$-$C_6$)-alkylene-N(R9)(R10), —(CO)—($C_1$-$C_6$)-alkyl, —($C_1$-$C_6$)-alkyl, $CF_3$, $OCF_3$, N(R9)(R10);

R3 H, ($C_1$-$C_6$)-alkyl, ($C_1$-$C_6$)-alkylene-aryl, —C(O)-aryl, ($C_1$-$C_6$)-alkylene-heterocycle, CO—($C_1$-$C_6$)-alkyl, where the aryl and heterocyclic radicals may be substituted one or more times by F, Cl, Br, ($C_1$-$C_6$)-alkyl, COOH, COO($C_1$-$C_6$)-alkyl, $CF_3$ or $OCF_3$;

R4, R5 independently of one another H, F, Cl, Br, ($C_1$-$C_6$)-alkyl, $CF_3$, $OCF_3$, $NO_2$, N(R9)(R10), CN, O—($C_1$-$C_6$)-alkyl, CO—($C_1$-$C_6$)-alkyl, COOH, ($C_1$-$C_6$)-alkylene-COOH, CON(R9)(R10), ($C_1$-$C_6$)-alkylene-CON(R9)(R10), COO($C_1$-$C_6$)-alkyl, ($C_1$-$C_6$)-alkylene-COO($C_1$-$C_6$)-alkyl, $S(O)O-2$-($C_1$-$C_6$)-alkyl, $S(O)_2$—N(R9)(R10), $CH_2OH$, $CH_2OCH_3$;

R6, R7 independently of one another H, F, Cl, Br, ($C_1$-$C_6$)-alkyl, cyclopropyl, tetrafluorocyclopropyl, difluorocyclopropyl; or R6 and R7 together form the group =$CH_2$;

R8 H, $CH_3$, $CF_3$, $CH_2OH$;

R9 H, ($C_1$-$C_4$)-alkyl;

R10 H, ($C_1$-$C_4$)-alkyl; or

R9 and R10 form together with the N atom to which they are bonded a 3-9 membered ring system;

and the physiologically tolerated salts thereof.

Preference is given to compounds of the formula I in which one or more radicals have the following meaning:

R1 aryl, ($C_1$-$C_6$)-alkyl, ($C_2$-$C_6$)-alkenyl, ($C_1$-$C_6$)-alkylene-aryl, heterocycle, ($C_1$-$C_6$)-alkylene-heterocycle, $CF_3$, $OCF_3$, CN, ($CH_2$)$_{1-6}$—OH, O—($C_1$-$C_6$)-alkyl, CO—($C_1$-$C_6$)-alkyl, C(O)O-alkyl, COOH, CON(R9)(R10), where the aryl radicals and the heterocyclic radicals may be substituted one or more times by F, Cl, Br, ($CH_2$)$_{0-2}$OH, ($C_1$-$C_6$)-alkyl, ($C_2$-$C_6$)-alkenyl, ($C_2$-$C_6$)-alkynyl, $CF_3$, $OCF_3$, N(R9)(R10), piperidinone, piperazine, piperazinone, N—($C_1$-$C_6$-alkylene)-piperazine, N—($C_1$-$C_6$-alkylene)-piperazinone, morpholine, thiomorpholine, $NO_2$, CN, O—($C_1$-$C_6$)-alkyl, $S(O)_{0-2}$—($C_1$-$C_6$)-alkyl, $SO_2$—N(R9)(R10), CO—($C_1$-$C_6$)-alkyl, —COOH, ($C_1$-$C_6$)-alkylene-COOH, —COO($C_1$-$C_6$)-alkyl, ($C_0$-$C_6$)-alkylene —COO ($C_1$-$C_6$)-alkyl, $C_3$-$C_{10}$-cycloalkyl, phenyl, where these piperidinone, piperazine, piperazinone, N—($C_1$-$C_6$-alkylene)-piperazine, N—($C_1$-$C_6$-alkylene)-piperazinone, morpholine, thiomorpholine and phenyl rings may be substituted one or more times by F, Cl, Br, ($CH_2$)$_{0-2}$OH, COOH, CN, $NO_2$, —O—($C_1$-$C_6$)-alkyl, —NH—O—($C_1$-$C_6$)-alkyl, —(CO)—NH—O—($C_1$-$C_6$)-alkylene-N(R9)(R10), —(CO)—($C_1$-$C_6$)-alkyl, —($C_1$-$C_6$)-alkyl, $CF_3$, $OCF_3$, N(R9)(R10);

R2 H, aryl, COOH, ($C_1$-$C_6$)-alkylene-COOH, —COO($C_1$-$C_6$)-alkyl, ($C_1$-$C_6$)-alkylene-COO($C_1$-$C_6$)-alkyl; ($C_1$-$C_6$)-alkyl, ($C_2$-$C_6$)-alkenyl, ($C_1$-$C_6$)-alkylene-aryl, heterocycle, ($C_1$-$C_6$)-alkylene-heterocycle, $CF_3$, $OCF_3$, CN, —(CH$_2$)$_{1-6}$—OH, O—(C$_1$-C$_6$)-alkyl, CO—(C$_1$-C$_6$)-alkyl, C(O)O-alkyl, COOH, CON(R9)(R10), where the aryl radicals and the heterocyclic radicals may be substituted one or more times by F, Cl, Br, (CH$_2$)$_{0-2}$OH, (C$_1$-C$_6$)-alkyl, (C$_2$-C$_6$)-alkenyl, (C$_2$-C$_6$)-alkynyl, CF$_3$, OCF$_3$, N(R9)(R10), piperidinone, piperazine, piperazinone, N—(C$_1$-C$_6$-alkylene)-piperazine, N—(C$_1$-C$_6$-alkylene)-piperazinone, morpholine, thiomorpholine, NO$_2$, CN, O—(C$_1$-C$_6$)-alkyl, S(O)$_{0-2}$—(C$_1$-C$_6$)-alkyl, SO$_2$—N(R9)(R10), CO—(C$_1$-C$_6$)-alkyl, —COOH, (C$_1$-C$_6$)-alkylene-COOH, —COO(C$_1$-C$_6$)-alkyl, (C$_1$-C$_6$)-alkylene-COO(C$_1$-C$_6$)-alkyl, C$_3$-C$_{10}$-cycloalkyl, phenyl;

R3 H, (C$_1$-C$_6$)-alkyl, (C$_1$-C$_6$)-alkylene-aryl, —C(O)-aryl, (C$_1$-C$_6$)-alkylene-heterocycle, CO—(C$_1$-C$_6$)-alkyl;

R4, R5 independently of one another H, F, Cl, Br, (C$_1$-C$_6$)-alkyl, CF$_3$, OCF$_3$, NO$_2$, N(R9)(R10), CN, O—(C$_1$-C$_6$)-alkyl, CO—(C$_1$-C$_6$)-alkyl, COOH, (C$_1$-C$_6$)-alkylene-COOH, —CON(R9)(R10), (C$_1$-C$_6$)-alkylene-CON(R9)(R10), COO(C$_1$-C$_6$)-alkyl, (C$_1$-C$_6$)-alkylene-COO(C$_1$-C$_6$)-alkyl, S(O)$_{0-2}$—(C$_1$-C$_6$)-alkyl, S(O)$_2$—N(R9)(R10), CH$_2$OH, CH$_2$OCH$_3$;

R6, R7 independently of one another H, F, Cl, Br, (C$_1$-C$_6$)-alkyl, cyclopropyl, tetrafluorocyclopropyl, difluorocyclopropyl; or R6 and R7 together form the group =CH$_2$;

R8 H, CH$_3$, CF$_3$, CH$_2$OH;

R9 H, (C$_1$-C$_4$)-alkyl;

R10 H, (C$_1$-C$_4$)-alkyl; or

R9 and R10 form together with the N atom to which they are bonded a 3-9 membered ring system;

and the physiologically tolerated salts thereof.

Particular preference is given to compounds of the formula I in which one or more radicals have the following meaning:

R1 phenyl, naphthyl, thionaphthyl, pyridyl, where phenyl, naphthyl, thionaphthyl and pyridyl may be substituted one or more times by F, Cl, Br, (CH$_2$)$_{0-2}$OH, (C$_1$-C$_6$)-alkyl, (C$_2$-C$_6$)-alkenyl, (C$_2$-C$_6$)-alkynyl, CF$_3$, OCF$_3$, N(R9)(R10), piperidinone, piperazine, piperazinone, N—(C$_1$-C$_6$-alkylene)-piperazine, N—(C$_1$-C$_6$-alkylene)-piperazinone, morpholine, thiomorpholine, NO$_2$, CN, O—(C$_1$-C$_6$)-alkyl, S(O)$_{0-2}$—(C$_1$-C$_6$)-alkyl, SO$_2$—N(R9)(R10), CO—(C$_1$-C$_6$)-alkyl, COOH, (C$_1$-C$_6$)-alkylene-COOH, COO(C$_1$-C$_6$)-alkyl, (C$_1$-C$_6$)-alkylene-COO(C$_1$-C$_6$)-alkyl, C$_3$-C$_{10}$-cycloalkyl, phenyl, where these piperidinone, piperazine, piperazinone, N—(C$_1$-C$_6$-alkylene)-piperazine, N—(C$_1$-C$_6$-alkylene)-piperazinone, morpholine, thiomorpholine and phenyl rings may be substituted one or more times by F, Cl, Br, (CH$_2$)$_{0-2}$OH, COOH, CN, NO$_2$, —O—(C$_1$-C$_6$)-alkyl, —NH—O—(C$_1$-C$_6$)-alkyl, —(CO)—NH—O—(C$_1$-C$_6$)-alkylene-N(R9)(R10), —(CO)—(C$_1$-C$_6$)-alkyl, —(C$_1$-C$_6$)-alkyl, CF$_3$, OCF$_3$, N(R9)(R10);

R2 H, (C$_1$-C$_6$)-alkyl, COOH, (C$_1$-C$_6$)-alkylene-COOH, —COO(C$_1$-C$_6$)-alkyl, (C$_1$-C$_6$)-alkylene-COO(C$_1$-C$_6$)-alkyl;

R3 H, (C$_1$-C$_6$)-alkyl, (C$_1$-C$_6$)-alkylene-aryl, —C(O)-aryl, (C$_1$-C$_6$)-alkylene-heterocycle, CO—(C$_1$-C$_6$)-alkyl;

R4, R5 H;

R6, R7 H;

R8 H;

R9 H, (C$_1$-C$_4$)-alkyl;

R10 H, (C$_1$-C$_4$)-alkyl;

and the physiologically tolerated salts thereof.

Very particular preference is given to compounds of the formula I in which one or more radicals have the following meaning:

R1 phenyl, where phenyl, naphthyl, thionaphthyl and pyridyl may be substituted one or more times by F, Cl, Br, (CH$_2$)$_{0-2}$OH, (C$_1$-C$_6$)-alkyl, (C$_2$-C$_6$)-alkenyl, (C$_2$-C$_6$)-alkynyl, CF$_3$, OCF$_3$, N(R9)(R10), piperidinone, piperazine, piperazinone, N—(C$_1$-C$_6$-alkylene)-piperazine, N—(C$_1$-C$_6$-alkylene)-piperazinone, morpholine, thiomorpholine, NO$_2$, CN, O—(C$_1$-C$_6$)-alkyl, S(O)$_{0-2}$—(C$_1$-C$_6$)-alkyl, SO$_2$—N(R9)(R10), CO—(C$_1$-C$_6$)-alkyl, COOH, (C$_1$-C$_6$)-alkylene-COOH, COO(C$_1$-C$_6$)-alkyl, (C$_1$-C$_6$)-alkylene-COO(C$_1$-C$_6$)-alkyl, C$_3$-C$_{10}$-cycloalkyl, phenyl, where these piperidinone, piperazine, piperazinone, N—(C$_1$-C$_6$-alkylene)-piperazine, N—(C$_1$-C$_6$-alkylene)-piperazinone, morpholine, thiomorpholine and phenyl rings may be substituted one or more times by F, Cl, Br, (CH$_2$)$_{0-2}$—OH, COOH, CN, NO$_2$, —O—(C$_1$-C$_6$)-alkyl, —NH—O—(C$_1$-C$_6$)-alkyl, —(CO)—NH—O—(C$_1$-C$_6$)-alkylene-N(R9)(R10), —(CO)—(C$_1$-C$_6$)-alkyl, —(C$_1$-C$_6$)-alkyl, CF$_3$, OCF$_3$, N(R9)(R10);

R2 H, (C$_1$-C$_6$)-alkyl, —C(O)O—(C$_1$-C$_6$)-alkyl, —(C$_1$-C$_6$)-alkylene-C(O)O—(C$_1$-C$_6$)-alkyl, —COOH, —(C$_1$-C$_6$)-alkylene-COOH;

R3 H, (C$_1$-C$_6$)-alkyl, (C$_1$-C$_6$)-alkylene-aryl, —C(O)-aryl, (C$_0$-C$_6$)-alkylene-heterocycle, CO—(C$_1$-C$_6$)-alkyl;

R4, R5 H;

R6, R7 H;

R8 H;

R9 H;

R10 H and the physiologically tolerated salts thereof.

For explanation:

the oxazole residue

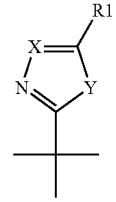

has when the meaning of the radicals is
X equal to C—R2;
Y equal to O;
the structure

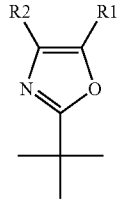

and when the meaning of the radicals is
X equal to O;
Y equal to C—R2;

the structure

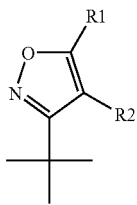

In addition, compounds in which X is equal to C—R2 and Y is equal to O are preferred.

The invention relates to compounds of the formula I in the form of their racemates, racemic mixtures and pure enantiomers, and to their diastereomers and mixtures thereof.

If radicals or substituents may occur more than once in the compounds of the formula I, they may all, independently of one another, have the stated meanings and be identical or different.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydro-chloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

An alkyl radical means a straight-chain or branched hydrocarbon chain having one or more carbons, such as, for example, methyl, ethyl, isopropyl, tert-butyl, hexyl.

The alkyl radicals may be substituted one or more times by suitable groups such as, for example:

F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)aryl, N(heterocycle)-CO—N(($C_1$-$C_6$)-alkyl)aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

An alkenyl radical means a straight-chain or branched hydrocarbon chain having two or more carbons and one or more double bonds, such as, for example, vinyl, allyl, pentenyl.

The alkenyl radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$-($CH_2$)$_n$-heterocycle, $SO_2$—$NH(CH_2)_n$-aryl, $SO_2$—$NH(CH_2)_n$-heterocycle, $SO_2$—$N(C_1\text{-}C_6)$-alkyl)$(CH_2)_n$-aryl, $SO_2$—$N(C_1\text{-}C_6)$-alkyl)$(CH_2)_n$-heterocycle, $SO_2$—$N((CH_2)_n$-aryl$)_2$, $SO_2$—$N((CH_2)_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—$(C_1\text{-}C_6)$-alkyl, $(C_1\text{-}C_6)$-alkyl, $NH_2$;

$C(NH)(NH_2)$, $NH_2$, NH—$(C_1\text{-}C_6)$-alkyl, $N((C_1\text{-}C_6)$-alkyl$)_2$, $NH(C_1\text{-}C_7)$-acyl, NH—CO—$(C_1\text{-}C_6)$-alkyl, NH—COO—$(C_1\text{-}C_6)$-alkyl, NH—CO-aryl, NH—CO-heterocycle, NH—COO-aryl, NH—COO-heterocycle, NH—CO—NH—$(C_1\text{-}C_6)$-alkyl, NH—CO—NH-aryl, NH—CO—NH-heterocycle, $N(C_1\text{-}C_6)$-alkyl —CO—$(C_1\text{-}C_6)$-alkyl, $N(C_1\text{-}C_6)$-alkyl —COO—$(C_1\text{-}C_6)$-alkyl, $N(C_1\text{-}C_6)$-alkyl —CO-aryl, $N(C_1\text{-}C_6)$-alkyl —CO-heterocycle, $N(C_1\text{-}C_6)$-alkyl —COO-aryl, $N(C_1\text{-}C_6)$-alkyl —COO-heterocycle, $N(C_1\text{-}C_6)$-alkyl —CO—NH—$(C_1\text{-}C_6)$-alkyl), $N(C_1\text{-}C_6)$-alkyl —CO—NH-aryl, $N(C_1\text{-}C_6)$-alkyl —CO—NH-heterocycle, $N((C_1\text{-}C_6)$-alkyl)-CO—N—$(C_1\text{-}C_6)$-alkyl$)_2$, $N((C_1\text{-}C_6)$-alkyl)-CO—N$((C_1\text{-}C_6)$-alkyl)aryl, $N((C_1\text{-}C_6)$-alkyl)-CO—N$((C_1\text{-}C_6)$-alkyl)-heterocycle, $N((C_1\text{-}C_6)$-alkyl)-CO—N-(aryl)$_2$, $N((C_1\text{-}C_6)$-alkyl)-CO—N-(heterocycle)$_2$, N(aryl)-CO—$(C_1\text{-}C_6)$-alkyl, N(heterocycle)-CO—$(C_1\text{-}C_6)$-alkyl, N(aryl)-COO—$(C_1\text{-}C_6)$-alkyl, N(heterocycle)-COO—$(C_1\text{-}C_6)$-alkyl, N(aryl)-CO-aryl, N(heterocycle)-CO-aryl, N(aryl)-COO-aryl, N(heterocycle)-COO-aryl, N(aryl)-CO—NH—$(C_1\text{-}C_6)$-alkyl), N(heterocycle)-CO—NH—$(C_1\text{-}C_6)$-alkyl), N(aryl)-CO—NH-aryl, N(heterocycle)-CO—NH-aryl, N(aryl)-CO—N—$(C_1\text{-}C_6)$-alkyl$)_2$, N(heterocycle)-CO—N—$(C_1\text{-}C_6)$-alkyl$)_2$, N(aryl)-CO—N$((C_1\text{-}C_6)$-alkyl)aryl, N(heterocycle)-CO—N$((C_1\text{-}C_6)$-alkyl)aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—$(C_1\text{-}C_6)$-alkyl, $(C_1\text{-}C_6)$-alkyl, $NH_2$, $NH(C_1\text{-}C_6)$-alkyl, $N((C_1\text{-}C_6)$-alkyl$)_2$, $SO_2$—$CH_3$, COOH, COO—$(C_1\text{-}C_6)$-alkyl, $CONH_2$.

An alkynyl radical means a straight-chain or branched hydrocarbon chain having two or more carbons and one or more triple bonds, such as, for example, ethynyl, propynyl, hexynyl.

The alkynyl radicals may be substituted one or more times by suitable groups such as, for example: F, Cl, Br, I, $CF_3$, $NO_2$, $N_3$, CN, COOH, COO$(C_1\text{-}C_6)$alkyl, $CONH_2$, $CONH(C_1\text{-}C_6)$alkyl, $CON[(C_1\text{-}C_6)$alkyl$]_2$, cycloalkyl, $(C_2\text{-}C_6)$-alkenyl, $(C_1\text{-}C_{10})$-alkyl, O—$(C_1\text{-}C_6)$-alkyl O—CO—$(C_1\text{-}C_6)$-alkyl, O—CO—$(C_1\text{-}C_6)$-aryl, O—CO—$(C_1\text{-}C_6)$-heterocycle;

$PO_3H_2$, $SO_3H$, $SO_2$—$NH_2$, $SO_2NH(C_1\text{-}C_6)$-alkyl, $SO_2N[(C_1\text{-}C_6)$-alkyl$]_2$, S—$(C_1\text{-}C_6)$-alkyl, S—$(CH_2)_n$-aryl, S—$(CH_2)_n$-heterocycle, SO—$(C_1\text{-}C_6)$-alkyl, SO—$(CH_2)_n$-aryl, SO—$(CH_2)_n$-heterocycle, $SO_2$—$(C_1\text{-}C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N(C_1\text{-}C_6)$-alkyl)$(CH_2)_n$-aryl, $SO_2$—$N(C_1\text{-}C_6)$-alkyl)$(CH_2)_n$-heterocycle, $SO_2$—$N((CH_2)_n$-aryl$)_2$, $SO_2$—$N((CH_2)_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—$(C_1\text{-}C_6)$-alkyl, $(C_1\text{-}C_6)$-alkyl, $NH_2$;

$C(NH)(NH_2)$, $NH_2$, NH—$(C_1\text{-}C_6)$-alkyl, $N((C_1\text{-}C_6)$-alkyl$)_2$, $NH(C_1\text{-}C_7)$-acyl, NH—CO—$(C_1\text{-}C_6)$-alkyl, NH—COO—$(C_1\text{-}C_6)$-alkyl, NH—CO-aryl, NH—CO-heterocycle, NH—COO-aryl, NH—COO-heterocycle, NH—CO—NH—$(C_1\text{-}C_6)$-alkyl, NH—CO—NH-aryl, NH—CO—NH-heterocycle, $N(C_1\text{-}C_6)$-alkyl —CO—$(C_1\text{-}C_6)$-alkyl, $N(C_1\text{-}C_6)$-alkyl —COO—$(C_1\text{-}C_6)$-alkyl, $N(C_1\text{-}C_6)$-alkyl —CO-aryl, $N(C_1\text{-}C_6)$-alkyl —CO-heterocycle, $N(C_1\text{-}C_6)$-alkyl —COO-aryl, $N(C_1\text{-}C_6)$-alkyl —COO-heterocycle, $N(C_1\text{-}C_6)$-alkyl —CO—NH—$(C_1\text{-}C_6)$-alkyl), $N(C_1\text{-}C_6)$-alkyl-CO—NH-aryl, $N(C_1\text{-}C_6)$-alkyl —CO—NH-heterocycle, $N((C_1\text{-}C_6)$-alkyl)-CO—N—$(C_1\text{-}C_6)$-alkyl$)_2$, $N((C_1\text{-}C_6)$-alkyl)-CO—N$((C_1\text{-}C_6)$-alkyl)aryl, $N((C_1\text{-}C_6)$-alkyl)-CO—N$((C_1\text{-}C_6)$-alkyl)-heterocycle, $N((C_1\text{-}C_6)$-alkyl)-CO—N-(aryl)$_2$, $N((C_1\text{-}C_6)$-alkyl)-CO—N-(heterocycle)$_2$, N(aryl)-CO—$(C_1\text{-}C_6)$-alkyl, N(heterocycle)-CO—$(C_1\text{-}C_6)$-alkyl, N(aryl)-COO—$(C_1\text{-}C_6)$-alkyl, N(heterocycle)-COO—$(C_1\text{-}C_6)$-alkyl, N(aryl)-CO-aryl, N(heterocycle)-CO-aryl, N(aryl)-COO-aryl, N(heterocycle)-COO-aryl, N(aryl)-CO—NH—$(C_1\text{-}C_6)$-alkyl), N(heterocycle)-CO—NH—$(C_1\text{-}C_6)$-alkyl), N(aryl)-CO—NH-aryl, N(heterocycle)-CO—NH-aryl, N(aryl)-CO—N—$(C_1\text{-}C_6)$-alkyl$)_2$, N(heterocycle)-CO—N—$(C_1\text{-}C_6)$-alkyl$)_2$, N(aryl)-CO—N$((C_1\text{-}C_6)$-alkyl)aryl, N(heterocycle)-CO—N$((C_1\text{-}C_6)$-alkyl)aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—$(C_1\text{-}C_6)$-alkyl, $(C_1\text{-}C_6)$-alkyl, $NH_2$, $NH(C_1\text{-}C_6)$-alkyl, $N((C_1\text{-}C_6)$-alkyl$)_2$, $SO_2$—$CH_3$, COOH, COO—$(C_1\text{-}C_6)$-alkyl, $CONH_2$.

An aryl radical means a phenyl, naphthyl-, biphenyl-, tetrahydronaphthyl-, alpha- or beta-tetralon-, indanyl- or indan-1-onyl radical.

The aryl radicals may be substituted one or more times by suitable groups such as, for example: F, Cl, Br, I, $CF_3$, $NO_2$, $N_3$, CN, COOH, COO$(C_1\text{-}C_6)$alkyl, $CONH_2$, $CONH(C_1\text{-}C_6)$alkyl, $CON[(C_1\text{-}C_6)$alkyl$]_2$, cycloalkyl, $(C_1\text{-}C_{10})$-alkyl, $(C_2\text{-}C_6)$-alkenyl, $(C_2\text{-}C_6)$-alkynyl, O—$(C_1\text{-}C_6)$-alkyl O—CO—$(C_1\text{-}C_6)$-alkyl, O—CO—$(C_1\text{-}C_6)$-aryl, O—CO—$(C_1\text{-}C_6)$-heterocycle;

$PO_3H_2$, $SO_3H$, $SO_2$—$NH_2$, $SO_2NH(C_1\text{-}C_6)$-alkyl, $SO_2N[(C_1\text{-}C_6)$-alkyl$]_2$, S—$(C_1\text{-}C_6)$-alkyl, S—$(CH_2)_n$-aryl, S—$(CH_2)_n$-heterocycle, SO—$(C_1\text{-}C_6)$-alkyl, SO—$(CH_2)_n$-aryl, SO—$(CH_2)_n$-heterocycle, $SO_2$—$(C_1\text{-}C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N(C_1\text{-}C_6)$-alkyl)$(CH_2)_n$-aryl, $SO_2$—$N(C_1\text{-}C_6)$-alkyl)$(CH_2)_n$-heterocycle, $SO_2$—$N((CH_2)_n$-aryl$)_2$, $SO_2$—$N((CH_2)_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—$(C_1\text{-}C_6)$-alkyl, $(C_1\text{-}C_6)$-alkyl, $NH_2$;

$C(NH)(NH_2)$, $NH_2$, NH—$(C_1\text{-}C_6)$-alkyl, $N((C_1\text{-}C_6)$-alkyl$)_2$, $NH(C_1\text{-}C_7)$-acyl, NH—CO—$(C_1\text{-}C_6)$-alkyl, NH—COO—$(C_1\text{-}C_6)$-alkyl, NH—CO-aryl, NH—CO-heterocycle, NH—COO-aryl, NH—COO-heterocycle, NH—CO—NH—$(C_1\text{-}C_6)$-alkyl, NH—CO—NH-aryl, NH—CO—NH-heterocycle, $N(C_1\text{-}C_6)$-alkyl —CO—$(C_1\text{-}C_6)$-alkyl, $N(C_1\text{-}C_6)$-alkyl —COO—$(C_1\text{-}C_6)$-alkyl, $N(C_1\text{-}C_6)$-alkyl —CO-aryl, $N(C_1\text{-}C_6)$-alkyl —CO-heterocycle, $N(C_1\text{-}C_6)$-alkyl —COO-aryl, $N(C_1\text{-}C_6)$-alkyl —COO-heterocycle, $N(C_1\text{-}C_6)$-alkyl —CO—NH—$(C_1\text{-}C_6)$-alkyl), $N(C_1\text{-}C_6)$-alkyl-CO—NH-aryl, $N(C_1\text{-}C_6)$-alkyl —CO—NH-heterocycle, $N((C_1\text{-}C_6)$-alkyl)-CO—N—$(C_1\text{-}C_6)$-alkyl$)_2$, $N((C_1\text{-}C_6)$-alkyl)-CO—N$((C_1\text{-}C_6)$-alkyl)aryl, $N((C_1\text{-}C_6)$-alkyl)-CO—N$((C_1\text{-}C_6)$-alkyl)-heterocycle, $N((C_1\text{-}C_6)$-alkyl)-CO—N-(aryl)$_2$, $N((C_1\text{-}C_6)$-alkyl)-CO—N-(heterocycle)$_2$, N(aryl)-CO—$(C_1\text{-}C_6)$-alkyl, N(heterocycle)-CO—$(C_1\text{-}C_6)$-alkyl, N(aryl)-COO—$(C_1\text{-}C_6)$-alkyl, N(heterocycle)-COO—$(C_1\text{-}C_6)$- alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)aryl, N(heterocycle)-CO—N(($C_1$-$C_6$)-alkyl)aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

A cycloalkyl radical means a ring system which comprises one or more rings, which is in saturated or partially unsaturated (with one or two double bonds) form and which is composed exclusively of carbon atoms, such as, for example, cyclopropyl, cyclopentyl, cyclopentenyl, cyclohexyl or adamantyl.

The cycloalkyl radicals radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)aryl, N(heterocycle)-CO—N(($C_1$-$C_6$)-alkyl)aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

Heterocycle or heterocyclic radical means rings and ring systems which, apart from carbon, also comprise heteroatoms such as, for example, nitrogen, oxygen or sulfur. Also included in this definition are ring systems in which the heterocycle or the heterocyclic radical is fused to benzene nuclei.

Suitable "heterocyclic rings" or "heterocyclic radicals" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl stands both for 2-, 3- and 4-pyridyl. Thienyl stands both for 2- and 3-thienyl. Furyl stands both for 2- and 3-furyl.

Also included are the corresponding N-oxides of these compounds, that is to say, for example, 1-oxy-2-, 3- or 4-pyridyl.

Also included are derivatives of these heterocycles which are benzo-fused one or more times.

The heterocyclic rings or heterocyclic radicals may be substituted one or more times by suitable groups such as, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)aryl, N(heterocycle)-CO—N(($C_1$-$C_6$)-alkyl)'aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n may be 0-6, where the aryl radical or heterocyclic radical may be substituted one to 3 times by F, Cl, Br, I, OH, CF$_3$, NO$_2$, CN, OCF$_3$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, COOH, COO—($C_1$-$C_6$)-alkyl, CONH$_2$.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg and 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropyl-methylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compound(s) of the formula (I) may also be administered in combination with other active ingredients.

Further active ingredients suitable for combination products are:

all antidiabetics mentioned in the Rote Liste 2003, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964, fast-acting insulins (see U.S. Pat. No. 6,221,633), GLP-1 derivatives such as, for example, those disclosed in WO 97/26265, WO 99/03861, WO 01/04156, WO 00/34331, WO 00/34332, WO 91/11457 and U.S. Pat. No. 6,380,357 and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor such as, for example, ezetimibe, tiqueside, pamaqueside.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in PCT/US 11833, PCT/US 11490, DE10142734.4.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with bile acid absorption inhibitor (see, for example, U.S. Pat. No. 6,245, 744 or U.S. Pat. No. 6,221,897), such as, for example, HMR 1741.

In one embodiment of the invention, the compounds of the formula I are administered in combination with a CETP inhibitor, such as, for example, JTT-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512), such as, for example, HMR1171, HMR1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein (a) antagonist, such as, for example, Cl-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl] methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]cyclohexyl-methyl}amide; hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chloro-phenyl)-2-oxoethyl]amide; (WO 01/91752)), orexin antagonists (e.g. 1-(2-methylbenzoxazol-6-yl)-3-[1,5]naphthyridin-4-ylurea; hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol; hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)); serotonin reuptake inhibitors (e.g. dexfenfluramine), mixed sertoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphatamine or amphetamine.

In one embodiment, the other active ingredient is an antihypertensive, such as, for example, an ACE inhibitor.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is regarded as falling within the protection conferred by the present invention.

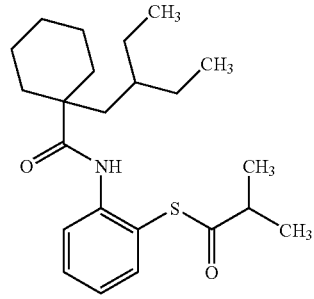

JTT-705

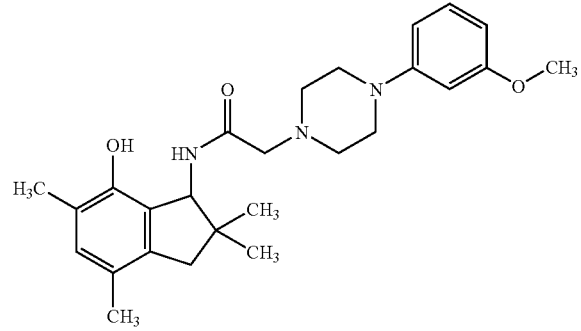

OPC-14117

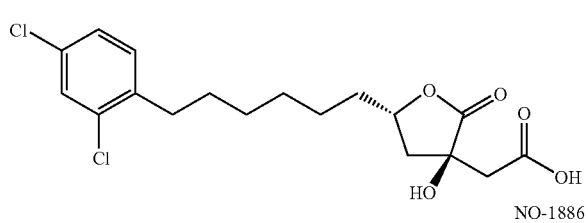

SB-204990

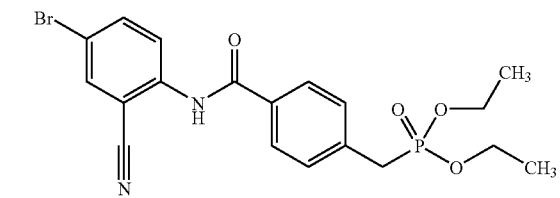

NO-1886

-continued
Cl-1027
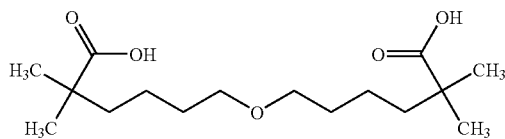
BMS-188494
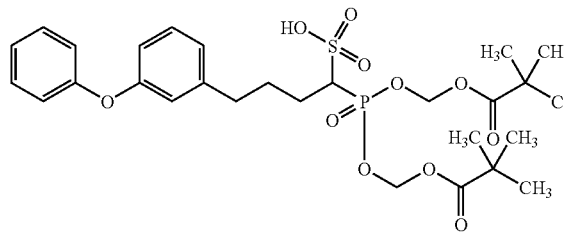
-continued
Gl 262570
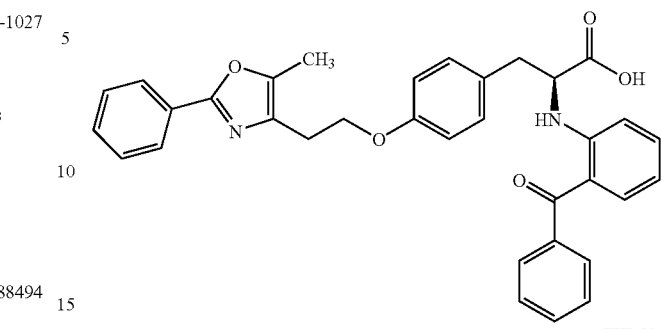
JTT-501
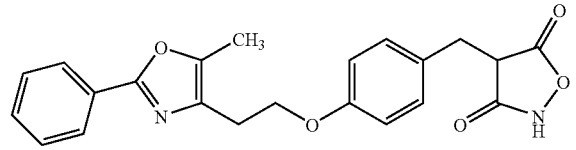
The examples listed below serve to illustrate the invention without, however, restricting it.
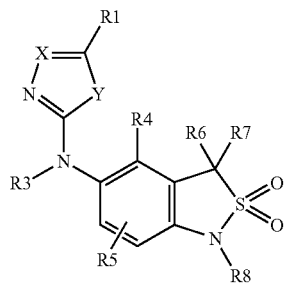
I
| Ex. | X | Y | R1 | R3 | R4 | R5 | R6 | R7 | R8 | m.p. |
|---|---|---|---|---|---|---|---|---|---|---|
| 1 | CH | O | 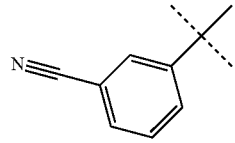 | H | H | H | H | H | H | |
| 2 | CH | O | 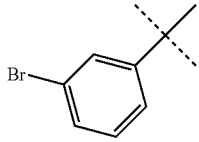 | H | H | H | H | H | H | |
| 3 | CH | O | 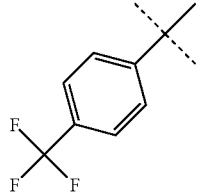 | H | H | H | H | H | H | |

-continued
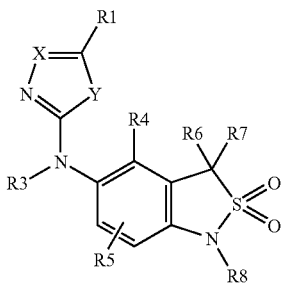
| Ex. | X | Y | R1 | R3 | R4 | R5 | R6 | R7 | R8 | m.p. |
|---|---|---|---|---|---|---|---|---|---|---|
| 4 | CH | O | 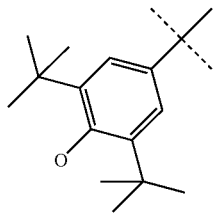 | H | H | H | H | H | H | |
| 5 | CH | O | 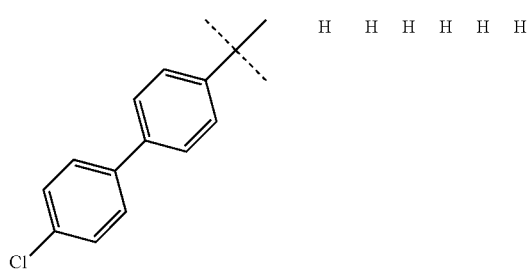 | H | H | H | H | H | H | |
| 6 | CH | O | 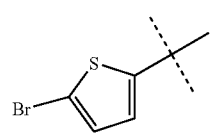 | H | H | H | H | H | H | |
| 7 | CH | O | 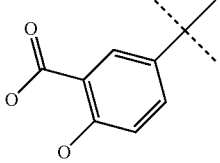 | H | H | H | H | H | H | |
| 8 | CH | O | 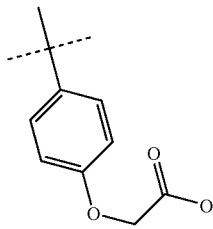 | H | H | H | H | H | H | |
| 9 | O— | C= | 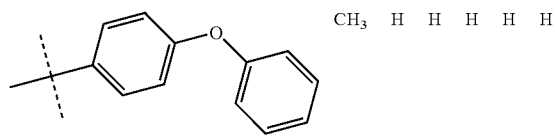 | $CH_3$ | H | H | H | H | H | |

The activity of the compounds was tested as follows:

Enzymatic test systems for detecting inhibition of a phosphatase

The compounds of the formula I were tested for their phosphatase-inhibiting effect in an in vitro assay. The enzyme preparation and the performance of the assay was carried out as follows.

Obtaining the Enzyme Preparation:

A) Cell Culture:
Sf9 cells (=*Spodoptera frugiperda* cell type; obtainable from invitrogen) are cultured in Grace's supplemented medium (Gibco-BRL) with 10% heat-inactivated fetal calf serum (Gibco-BRL) in spinner flasks at 28° C. in accordance with the protocol of Summers and Smith (A Manual for Methods for Baculoviruns Vectors and Insect Culture Procedures [Bulletin No. 15555]. Texas A & M University, Texas Agricultural Experiment Station, College Station, Tex., 1987).

Construction of recombinant Baculovirus transfer vectors: cDNA coding for the regulatory and catalytic domains of human PTP1B, but without the carboxy-terminal hydrophobic region (corresponding to 1-299 aa) was obtained by polymerase chain reaction via primers with attached cloning sites and suitable cDNA templates (obtainable for example from invitrogen) and then cloned into baculovirus expression vectors (Amersham Pharmacia Biotech.). The recombinant baculoviruses were prepared with the aid of the Bac-to-Bac baculovirus expression system (obtainable from Gibco-BRL). The gene was cloned into the pFASTBAC donor plasmid (obtainable from Life Technologies). The resulting plasmid was transformed into competent DH10BAC *Escherichia coli* cells (obtainable from Life Technologies). After transposition and antibiotic selection, the recombinant plasmid DNA was isolated from selected *E. coli* colonies and then used for the transfection of Sf9 insect cells. The virus particle in the supernatant medium was amplified three times up to a viral stock volume of 500 ml.

B) Production of Recombinant Protein:
Baculovirus infection of a 500 ml spinner culture of Sf9 cells was essentially carried out as described by Summers and Smith (see above). Sf9 cells at a density of $1-3 \times 10^6$ cells/ml were pelleted by centrifugation at 300 g for 5 min, the supernatant was removed, and the cells were resuspended in a density of $1 \times 10^7$ cells/ml in a suitable recombinant viral stock (MOI 10). After careful shaking at room temperature for 1.5 h, fresh medium was added in order to achieve a cell density of $1 \times 10^6$ cells/ml. The cells were then cultured in suspension at 28° C. for suitable periods after postinfection.

C) Cellular Fractionation and Complete Cell Extracts of Infected Sf9 Cells:
After the postinfection, aliquots were subjected to an analysis of protein expression by SDS-PAGE and Western blot analysis. The cellular fractionation was carried out as described (Cromlish, W. and Kennedy, B. Biochem. Pharmacol. 52: 1777-1785, 1996). Complete cell extracts were obtained from 1 ml aliquots of the infected Sf9 cells after certain times postinfection. The pelleted cells (300×g, 5 min) were washed once in phosphate-buffered saline (4° C.), resuspended in 50 µl of water and disrupted by repeated freezing/thawing. Protein concentrations were determined with the aid of the Bradford method and bovine serum albumin as standard.

Assay Procedure:

A) Dephosphorylation of a Phosphopeptide:
This assay is based on the release of phosphate from a consensus substrate peptide which is detected in the nanomolar concentration range by the malachite green/ammonium molybdate method (Lanzefta, P. A., Alvarez, L. J., Reinach, P. S., Candia, O. A. Anal Biochem. 100: 95-97, 1979) adapted for the microtiter plate format. The dodecatrisphosphopeptide TRDIYETDYYRK (Biotrend, Cologne) corresponds to amino acids 1142-1153 of the catalytic domain of the insulin receptor and is (auto)phosphorylated on tyrosine residues 1146, 1150 and 1151. The recombinant hPTP1B was diluted with assay buffer (40 mM Tris/HCl, pH 7.4, 1 mM EDTA, 20 mM DTT), equivalent to an activity of 1000-1500 nmol/min/mg of protein and (a 20 µl portion) then preincubated (15 min, 30° C.) in the absence or presence of test substance (5 µl) in the desired concentration (final concentration of DMSO 2% max.) in a total volume of 90 µl (assay buffer). To start the dephosphorylation reaction, the peptide substrate (10 µl, prewarmed to 30° C.) was added to the preincubated enzyme preparation with or without test substance (final concentration 0.2-200 µM) and the incubation was continued for 1 h. The reaction was stopped by adding 100 µl of malachite green hydrochloride (0.45%, 3 parts), ammonium molybdate tetrahydrate (4.2% in 4 N HCl, 1 part) and 0.5% Tween 20 as stop solution. After incubation at 22° C. for 30 min to develop the color, the absorption at 650 nm was determined using a microtiter plate reader (molecular devices). Samples and blanks were measured in triplicate. The PTP1B activity was calculated as nanomoles of liberated phosphate per min and mg of protein with potassium phosphate as standard. The inhibition of the recombinant hPTP1B by test substances was calculated as a percentage of the phosphatase control. The $IC_{50}$ values show significant agreement with a four-parameter nonlinear logistic regression curve.

B) Cleavage of p-nitrophenyl Phosphate:
This assay is based on the change in absorption of the non-physiological substrate p-nitrophenyl phosphate during cleavage to give nitrophenol under standard conditions (Tonks, N. K., Diltz, C. D:, Fischer, E. H. J. Biol. Chem. 263: 6731-6737, 1988; Burke T. R., Ye, B., Yan, X. J., Wang, S. M., Jia, Z. C., Chen, L., Zhang, Z. Y., Barford, D. Biochemistry 35: 15989-15996, 1996). The inhibitors are pipetted in suitable dilution into the reaction mixtures which contain 0.5-5 mM p-nitrophenyl phosphate. The following buffers were used (total volume 100 µl): (a) 100 mM sodium acetate (pH 5.5), 50 mM NaCl, 0.1% (w/v) bovine serum albumin, 5 mM glutathione, 5 mM DTT, 0.4 mM EGTA and 1 mM EDTA; (b) 50 mM Hepes/KOH (pH 7.4), 100 mM NaCl, 0.1% (w/v) bovine serum albumin, 5 mM glutathione, 5 mM DTT and 1 mM EDTA. The reaction was started by adding enzyme and carried out in microtiter plates at 25° C. for 1 h. The reaction was stopped by adding 100 µl of 0.2 N NaOH. The enzyme activity was determined by measuring the absorption at 405 nm with suitable corrections for absorption of the test substances and of p-nitrophenyl phosphate. The results were expressed as percentage of the control by comparing the amount of p-nitrophenol formed in the test substance-treated samples (nmol/min/mg of protein) with the amount in the untreated samples. The average and the standard deviation were calculated, and the IC50 values were determined by regression analysis of the linear portion of the inhibition curves.

TABLE 2

Biological activity

| Ex. | IC-50 (µM) |
|---|---|
| 1 | 7.30 |
| 2 | 12.6 |
| 3 | 15.72 |
| 4 | 6.12 |
| 5 | 2.16 |
| 6 | 9.44 |
| 7 | 162 |
| 8 | 290 |
| 9 | 9.15 |

It is evident from the table that the compounds of the formula I inhibit the activity of phosphotyrosine phosphatase 1B (PTP1B) and thus are very suitable for lowering the blood glucose level. They are therefore suitable in particular for the treatment of type I and II diabetes, of insulin resistance, of dyslipidemias, of the metabolic syndrome/syndrome X, of pathological obesity and for weight reduction in mammals.

Compounds of the formula I are also suitable, because of their inhibition of PTP1B, for the treatment of hyperglycerimia, high blood pressure, atherosclerosis, dysfunctions of the immune system, autoimmune diseases, allergic diseases such as, for example, asthma, arthritis, osteoarthritis, osteoporosis, proliferation disorders such as cancer and psoriasis, diseases with reduced or increased production of growth factors, hormones or cytokines, which induce the release of growth hormones.

The compounds are also suitable for the treatment of disorders of the nervous system such as, for example, Alzheimer's or multiple sclerosis.

The compounds are also suitable for the treatment of disturbances of well-being and other psychiatric indications such as, for example, depressions, anxiety states, anxiety neuroses, schizophrenia, for the treatment of disorders associated with the circadian rhythm and for the treatment of drug abuse.

They are additionally suitable for treatment of sleep disorders, sleep apnea, female and male sexual disorders, inflammations, acne, pigmentation of the skin, disorders of steroid metabolism, skin diseases and mycoses.

The preparation of example 4 in table 1 is described in detail below, and the other compounds of the formula I were obtained analogously:

EXPERIMENTAL PART

A solution of (2-fluoro-5-nitrobenzyl bromide (30 g, 0.128 mol) in acetonitrile (250 ml) is added to a solution of $Na_2SO_3$ (27.36 g, 0.128 mol) in $H_2O$ (375 ml), and the mixture is stirred at RT for 24 h. The solvent is distilled off in vacuo, the residue is stirred with 100 ml of isopropanaol, and the solid is filtered off and washed with a little isopropanol and diethyl ether.

Yield: 28.15 g

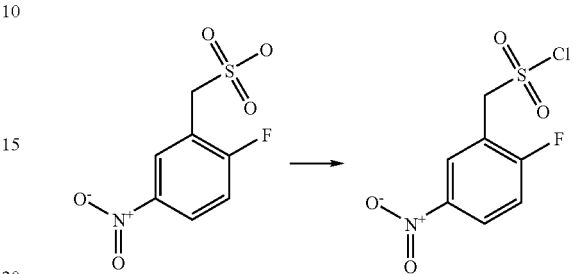

The sodium salt of the sulfonic acid 1 (35.19 g, 0.1368 mol) is introduced into $POCl_3$ (430 ml), and then $PCl_5$ (28.78 g, 0.137 mol) is added. The mixture is heated under reflux for 5 h. For workup, it is concentrated in vacuo, and the residue is poured onto ice/water. The reaction product separates out as a pale yellow solid, which is filtered off.

Yield: 30.3 g

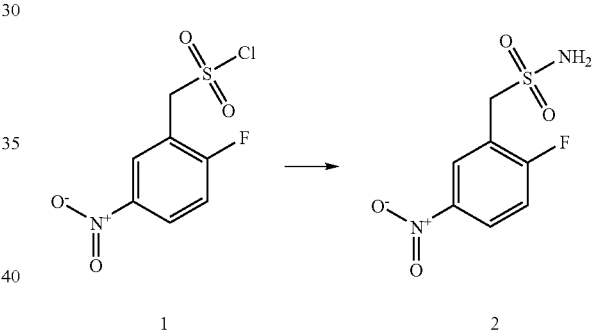

A solution of the sulfonyl chloride 1 (30.3 g, 0.12 mol) in $CH_2Cl_2$ (125 ml) is added dropwise to concentrated ammonia (90 ml, 1.2 mol) at RT. The mixture is stirred at RT for 20 h and then acidified to pH 1 with HCl (1 N). The organic phase is then distilled off under reduced pressure, during which the reaction product separates out as a pale yellow solid. The reaction product is then filtered off.

Yield 25.01 g (89.4%).

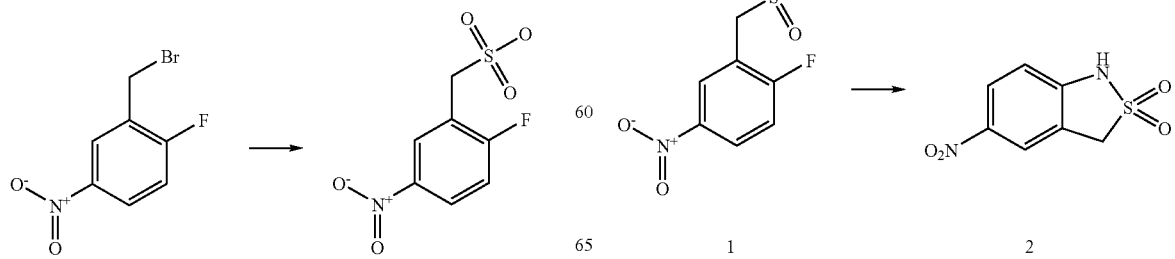

Diazabicycloundecene (34.1 g, 33.42 ml, 0.22 mol) is added to a solution of compound 1 (25 g, 0.107 mol) in DMF (1 l) at RT, and the reaction mixture is stirred at 130° C. for 2 h. The solvent is then distilled off in vacuo, the residue is mixed with water (400 ml), HCl (2N, 400 ml) is added, and the product is extracted several times with dichloromethane. The combined organic phases are dried (Na$_2$SO$_4$) and the solvent is distilled off under reduced pressure. The remaining residue is stirred with a little cold isopropanol, and the reaction product is then filtered off.

Yield: 20.8 g (91.3%).

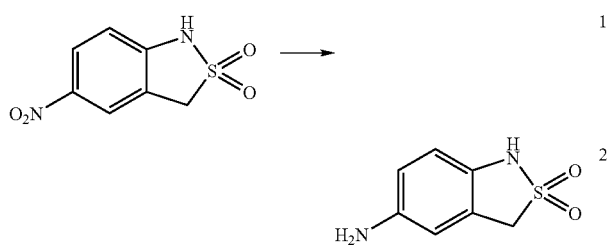

535 mg of the nitro compound are dissolved in 100 ml of methanol/THF mixture (1:1), and 5 mol % Pd (10% on activated carbon) is added. Hydrogenation is then carried out with hydrogen in a hydrogenation apparatus at room temperature until hydrogen uptake ceases (reaction time: 1 h).

For workup, the catalyst is filtered off through Celite® filtration aid, and the filtrate is concentrated under reduced pressure. The oily residue is stirred with a little diethyl ether, filtered off, washed with n-pentane and dried in vacuo.

Yield: 397 mg (86% of theory)

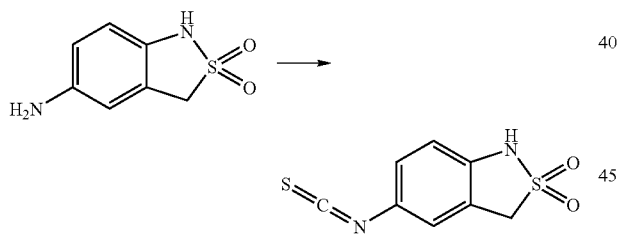

1.84 g (10 mmol) of the aniline prepared above are suspended in 240 ml of absolute dichloromethane and, while stirring at 20° C., 2.55 g (11 mmol) of 1,1'thiocarbonyldi-2 (1H)-pyridone are added. The reaction mixture is stirred at 20° C. for 5 h.

For workup, the reaction mixture is washed 3 times with 50 ml of water, and the organic phase is subsequently dried with Na$_2$SO$_4$ and filtered off from the desiccant.

Removal of the solvent under reduced pressure results in a pale yellow oil which crystallizes after addition of a little diethyl ether.

2.12 (9.4 mmol) of yellowish crystals are obtained; yield 94% of theory. MS (ES+): 227.2

1H-NMR (500 MHz, d$_6$-DMSO): δ=4.57 (s, 2H), 6.85 (d, J=8.56 Hz, 1H), 7.33 (ps d, J=8.56 Hz, 1H), 7.40 (ps s, 1H), 10.84 (br s, 1H)

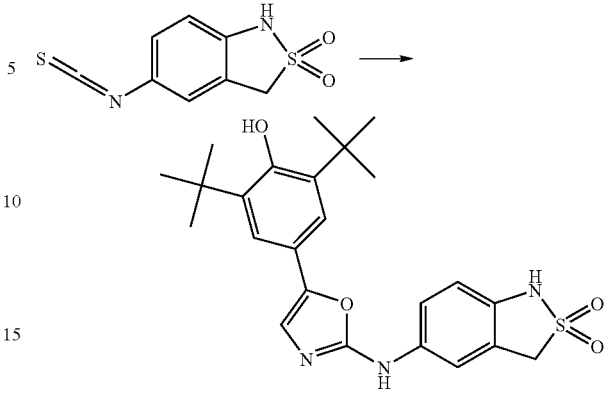

226 mg (1 mmol) of the isothiocyanate prepared above are dissolved in 10 ml of abs. tetrahydrofuran and, while stirring, 339 mg (1.5 mmol) of 2-azido-1-[3,5-di(tert-butyl)-4-hydroxyphenyl]ethan-1-one, prepared from 2-bromo-1-[3,5-di (tert-butyl)-4-hydroxyphenyl]ethan-1-one by reaction with sodium azide in DMF as solvent, and 315 mg (1.2 mmol) of triphenylphosphine are added. The reaction mixture is heated with the solvent refluxing for 1 h.

For workup, the reaction solution is concentrated under reduced pressure, and the remaining oily residue is chromatographed by chromatography on silica gel (40-63µ, from Merck) with ethyl acetate/heptane, mixing ratio 1:1, as mobile phase.

Yield 288 mg (63% of theory) MS (ES+): 455.99

1H-NMR (500 MHz, d$_6$-DMSO): δ=1.42 (s, 18H), 4.64 (s, 2H), 6.82 (d, J=8.6 Hz, 1H), 7.15 (s, 1H), 7.22 (s, 1H), 7.31 (s, 2H), 7.48 (dd, J=8.6 and 2.1 Hz, 1H), 7.70 (d, J=2.1 Hz, 1H), 10.11 (s, 1H), 10.15 (s, 1H)

What is claimed is:

1. A compound selected from the compounds of formula I

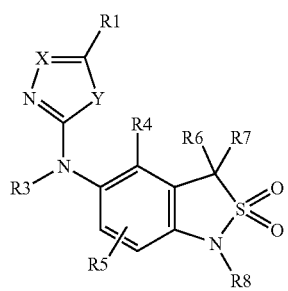

wherein:

X is O or C—R2;

Y is O or C—R2, with the case stipulation that when X or Y is O, the other is C—R2;

R1 is phenyl or thienyl wherein the phenyl and thienyl radicals may be substituted one or more times by a substituent selected from F, Cl, Br, (CH$_2$)$_{0-2}$OH, (C$_1$-C$_6$)-alkyl, (C$_2$-C$_6$)-alkenyl, (C$_2$-C$_6$)-alkynyl, CF$_3$, OCF$_3$, N(R9)(R10), NO$_2$, CN, O—(C$_1$-C$_6$)-alkyl, S(O)$_{0-2}$-(C$_1$-C$_6$)-alkyl, SO$_2$-N(R9)(R10), CO—(C$_1$-C$_6$)-alkyl, —COOH, (C$_1$-C$_6$)-alkylene-COOH, COO (C$_1$-C$_6$)-alkyl, (C$_1$-C$_6$)-alkylene-COO(C$_1$-C$_6$)-alkyl, (C$_3$-C$_{10}$)-cycloalkyl, and phenyl R2 is selected from the group consisting of H, F, Cl, Br, and $(C_1-C_6)$-alkyl, wherein said $(C_1-C_6)$-alkyl may be substituted with a substituent selected from F, Cl, and Br;

R3 is selected from the group consisting of H, F, Cl, Br, and $(C_1-C_6)$-alkyl, wherein said $(C_1-C_6)$-alkyl may be substituted with a substituent selected from F, Cl, and Br;

R4 and R5, independently of one another, are selected from the group consisting of: H, F, Cl, Br, and $(C_1-C_6)$-alkyl, wherein said $(C_1-C_6)$-alkyl may be substituted with a substituent selected from F, Cl and Br;

R6 and R7, independently of one another, are selected from the group consisting of: H, F, Cl, Br, and $(C_1-C_6)$-alkyl, or, R6 and R7 together form $CH_2$;

R 8 is selected from H, $CH_3$, $CF_3$ and $CH_2OH$;

R 9 is selected from H and $(C_1-C_4)$-alkyl;

R 10 is selected from H and $(C_1-C_4)$-alkyl;

or a physiologically tolerated salt thereof.

2. A compound of formula I as claimed in claim 1, wherein:

R1 is phenyl, which phenyl may be substituted one or more times by a substituent F, Cl, Br, $(CH_2)_{0-2}OH$, $(C_1-C_6)$-alkyl, $(C_2-C_6)$-alkenyl, $(C_2-C_6)$-alkynyl, $CF_3$, $OCF_3$, $N(R9)(R10)$, $NO_2$, CN, $O-(C_1-C_6)$-alkyl, $S(O)_{0-2}-(C_1-C_6)$-alkyl, $SO_2-N(R9)(R10)$, $CO-(C_1-C_6)$-alkyl, COOH, $(C_1-C_6)$-alkylene-COOH, $COO(C_1-C_6)$-alkyl, $(C_1-C_6)$-alkylene-COO$(C_1-C_6)$-alkyl, $C_3-C_{10}$-cycloalkyl, phenyl R2 is selected from H, F, Cl, Br, and $(C_1-C_6)$-alkyl, wherein said $(C_1-C_6)$-alkyl, may be substituted with a substituent selected from F, Cl, and Br;

R3 is selected from H, F, Cl, Br, and $(C_1-C_6)$-alkyl, wherein said $(C_1-C_6)$-alkyl may be substituted with a substituent selected from F, Cl, and Br;

R4, R5, R6, R7, R8, R9, and R10 are each H;

or a physiologically tolerated salts thereof.

3. A pharmaceutical composition comprising one or more of the compounds as claimed in claim 1.

4. A pharmaceutical composition comprising one or more of the compounds as claimed in claim 1 and at least one other active ingredient.

5. A pharmaceutical composition as claimed in claim 4, wherein the other active ingredient comprises one or more anti-diabetics, hypoglycemic active ingredients, HMGCoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, lipase inhibitors, insulins, sulfonylureas, biguanides, meglitinides, thiazolidinediones, α-glucosidase inhibitors, active ingredients which act on the ATP-dependent potassium channel of the beta cells, CART agonists, NPY agonists, MC4 agonists, orexin agonists, H3 agonists, TNF agonists, CRF agonists, CRF BP antagonists, urocortin agonists, β3 agonists, MSH (melanocyte-stimulating hormone) agonists, CCK agonists, serotonin reuptake inhibitors, mixed sertoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists (bromocriptine, Doprexin), lipase/amylase inhibitors, PPAR modulators, RXR modulators or TR-β agonists or amphetamines.

6. A method for reducing blood glucose comprising administering to a patient in need thereof an effective amount of a compound of claim 1.

7. A method for the treatment of type II diabetes comprising administering to a patient in need thereof an effective amount of a compound of claim 1.

8. A method for the treatment of insulin resistance comprising administering to a patient in need thereof an effective amount of a compound of claim 1.

9. A pharmaceutical composition of claim 3 which further comprises a pharmaceutically suitable carrier.

* * * * *